Feb. 19, 1974 R. E. DANIELSON Plant Pat. 3,486
CHRYSANTHEMUM PLANT
Filed Aug. 16, 1972
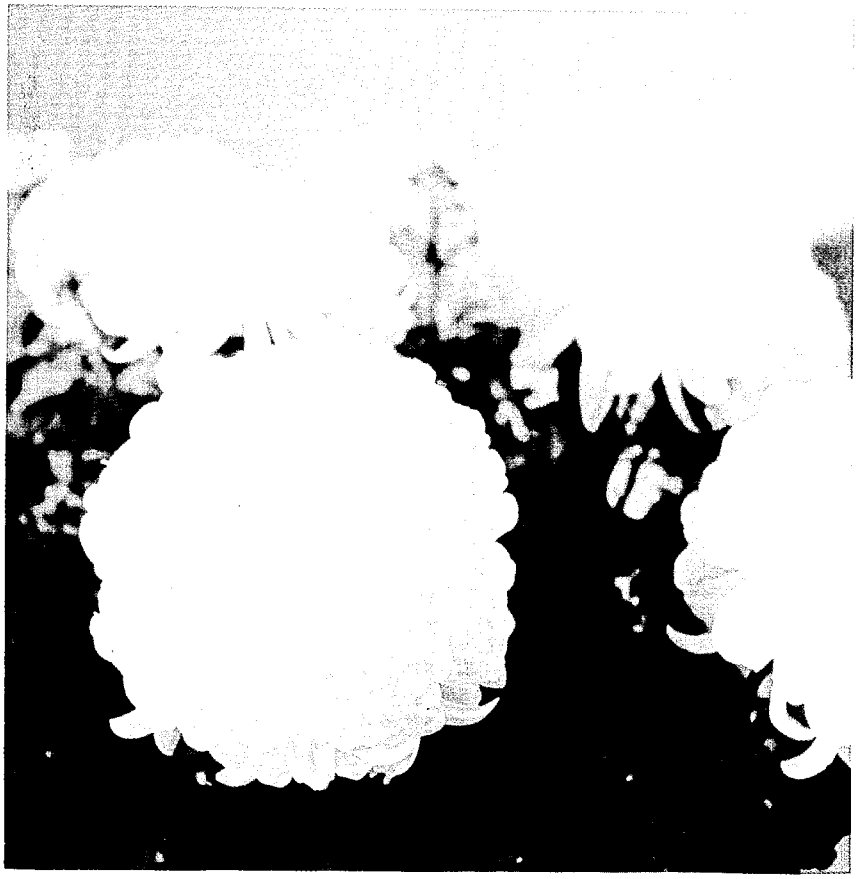
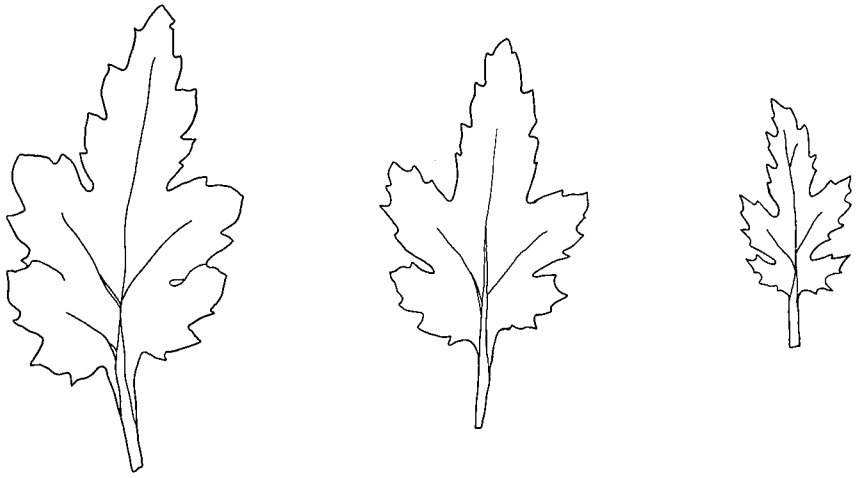

United States Patent Office

Plant Pat. 3,486

Patented Feb. 19, 1974

3,486

CHRYSANTHEMUM PLANT

Robert E. Danielson, West Chicago, Ill., assignor to Pan-American Plant Company, Chicago, Ill.

Filed Aug. 16, 1972, Ser. No. 281,170

Int. Cl. A01h 5/00

U.S. Cl. Plt.—78 1 Claim

ABSTRACT OF THE DISCLOSURE

A new irradiation mutation of the variety May Shoesmith (unpatented) having a very large globular flower of the standard incurved type and a deep yellow color. This variety has an eleven-week response, can be flowered the year around with photoperiod control, and is best suited for wintertime greenhouse culture.

BACKGROUND OF THE NEW PLANT

This new variety was discovered by me in June 1971 as a sport resulting from a radiation program carried on to develop new colors of the variety May Shoesmith (unpatented). This sport was asexually propagated under my direction at West Chicago, Ill., and has been found to be very similar in response and growth characteristics to its parent variety. Subsequent propagation of this new variety, by vegetative cuttings, at West Chicago, Ill., and at Cortez, Fla., has shown the novel color of this variety to be firmly fixed and to hold true from generation to generation.

DESCRIPTION OF THE DRAWING

My new variety of chrysanthemum plant is illustrated by the accompanying drawings in which the form and color of the blooms are shown by photographic rendition, the colors being as true as is reasonably possible by conventional photographic procedures, and in which the distinctive configuration of the leaves is shown by pen-and-ink drawing.

DESCRIPTION OF THE NEW PLANT

The following is a detailed description of my new variety of chrysanthemum plant with color designations according to Robert F. Wilson's Horticultural Colour Chart issued by The British Colour Council in collaboration with The Royal Horticultural Society of London, England.

*The plant*

Origin: Sport

Parentage: May Shoesmith (unpatented). This plant is an irradiation mutation

Classification:

*Botanic.*—*Chrysanthemum morifolium*

*Commercial.*—Standard incurved

Form: Perennial herbaceous bush

Height: 2 to 4 feet

Growth: Terminal. Vigorous, sturdy and upright with good strength

Branching: Branching occurs under natural conditions

Foliage: Abundant, producing 27 leaves on a 3-foot stem

*Leaf size.*—Mature leaf—5½ inches long by 3⅜ inches wide

*Shape.*—Lanceolate, lobed and serrated

*Color.*—Upper side—Spinch Green 0960. Under side—Spinch Green 0960/2

*Venation.*—Pinnate

*Petioles.*—1½ inches long

*The bud*

Form: Globular and oval in appearance from side view

Size: ½ inch in diameter and ⅜ inch in depth

Opening rate: Slow. 4 weeks to full sized flower

Color:

*When phyllaries first divide.*—Primrose Yellow 601/1

*When florets begin to unfurl.*—Dresden Yellow 64

Phyllaries: The outside of the receptacle bears many distinct involucral bracts which stand up and are spear shaped

*Color.*—Inside—Scheeles Green 860. Outside—Scheeles Green 860

*Surface aspect.*—Canescent

Calyx: Represented by tiny bristles arising from the top of the ovary and often it is absent Peduncle: Erect and from 3 to 4 inches long

*Surface aspect.*—Canescent

*The flower*

Response: 11-weeks. This variety can be flowered the year around with photoperiod control Recommended flowering: October 15 to May 15

Natural season flowering: Mid-November

Blooms: Standard incurved flower type

*Borne.*—A head of many florets borne on a single receptacle

*Size.*—Very large. 6½ inches in diameter and 4½ inches in depth

*Shape.*—Flat and round at outset becoming more globular as the florets develop

*Florets.*—Very many in number. Form: Linear with obtuse apex. Color: Outer florets—Dresden Yellow 64/2 with base of Uranium Green 63; inside florets—Dresden Yellow 64/2; reverse sides of florets—Dresden Yellow 64/1. Firmness: Medium. Appearance: Satiny

*Peduncle.*—Sturdy and erect—3 to 4 inches long

*Color.*—Pod Green 061/1

Persistence: Florets hang on and dry

Effect of weather: This new variety is recommended only for greenhouse culture

Lasting quality:

*On plant.*—3 to 4 weeks

*As cut flowers.*—2 to 3 weeks

*Reproductive organs*

Stamens: 5 in number arranged connately by their anthers to form a cylinder about the style Filaments:

*Length.*—¼ inch

*Color.*—Light Yellow

*Pollen.*—Color—Yellow

Pistils: One for each ray floret

*Style.*—Length—5/16 inch

*Stigmas.*—Color—Yellow

Ovaries: Inferior, bicarpellate

This new variety of chrysanthemum plant is similar to the variety Yellow May Shoesmith (Plant Pat. 3,280), but produces a much deeper yellow and more uniformly formed flower than Yellow May Shoesmith. This variety with its eleven-week response is most suited for wintertime culture in greenhouse, however, it still can be raised and flowered the year around. It produces large, well formed flowers, flowering with a very even response and producing very few culls.

I claim:

1. A new and distinct variety of chrysanthemum plant, substantially as herein shown and described, characterized by its very large, bright yellow blooms, its excellent production of well formed flowers, flowering with a very even eleven-week response and producing very few culls.

No references cited.

ROBERT E. BAGWILL, Primary Examiner